(12) United States Patent
Kerth et al.

(10) Patent No.: US 10,765,363 B2
(45) Date of Patent: Sep. 8, 2020

(54) HEADGEAR FOR DRY ELECTROENCEPHALOGRAM SENSORS

(71) Applicants: Trevor Austin Kerth, London (GB); Yu Mike Chi, San Diego, CA (US); Aileen Ngoc Tran, San Diego, CA (US)

(72) Inventors: Trevor Austin Kerth, London (GB); Yu Mike Chi, San Diego, CA (US); Aileen Ngoc Tran, San Diego, CA (US)

(73) Assignee: Cognionics, Inc., San Diego, CA (US)

( * ) Notice: Subject to any disclaimer, the term of this patent is extended or adjusted under 35 U.S.C. 154(b) by 555 days.

(21) Appl. No.: 15/299,953

(22) Filed: Oct. 21, 2016

(65) Prior Publication Data

US 2018/0092599 A1    Apr. 5, 2018

Related U.S. Application Data

(63) Continuation-in-part of application No. 15/300,992, filed on Sep. 30, 2016, now abandoned.

(51) Int. Cl.
*A61B 5/00* (2006.01)
*A61B 5/0478* (2006.01)
*A42B 1/24* (2006.01)

(52) U.S. Cl.
CPC ............ *A61B 5/6803* (2013.01); *A42B 1/242* (2013.01); *A61B 5/0478* (2013.01); *A61B 5/7225* (2013.01); *A61B 2562/04* (2013.01)

(58) Field of Classification Search
CPC ... A61B 5/6803; A61B 5/0476; A61B 5/0478; A61B 5/7225; A61B 2562/04; A42B 1/242

USPC .......................................... 600/383, 544, 545
See application file for complete search history.

(56) References Cited

U.S. PATENT DOCUMENTS

| | | | | |
|---|---|---|---|---|
| 6,154,669 A | * | 11/2000 | Hunter | A61B 5/0478 600/383 |
| 2007/0106169 A1 | * | 5/2007 | Fadem | A61B 5/04845 600/544 |
| 2008/0013777 A1 | * | 1/2008 | Park | A61B 5/0059 381/384 |

(Continued)

FOREIGN PATENT DOCUMENTS

| | | |
|---|---|---|
| DE | 102010017415 A1 | 12/2011 |
| WO | WO 2014/020554 A1 | 2/2014 |
| WO | WO-2014020554 A1 * | 2/2014 ........... A61B 5/0478 |

*Primary Examiner* — Linda C Dvorak
*Assistant Examiner* — James A Cipriano
(74) *Attorney, Agent, or Firm* — Edward W. Callan (57) ABSTRACT

A headgear for placing sensors on a subject's head includes a centerpiece; a plurality of arms attached to and radiating outward and generally downward from the centerpiece; and sensor tips attached to the dorsal ends of at least some of the arms. At least one of the plurality of arms is a lower arm that is elastic and/or spring-like. When the headgear is placed on a subject's head, the at least one lower arm is so disposed in relation to the maximum circumference of the subject's head that the at least one lower arm must be bent outward for placement of the headgear on the subject's head and thereby provide a reactive force toward the head that causes the at least one lower arm to grasp at least a portion of the head that is at and/or below the maximum circumference of the head.

15 Claims, 9 Drawing Sheets

(56) References Cited

U.S. PATENT DOCUMENTS

| | | | |
|---|---|---|---|
| 2011/0004089 A1 | 1/2011 | Chou | |
| 2011/0319975 A1* | 12/2011 | Ho | A61N 1/0408 |
| | | | 607/139 |
| 2013/0066185 A1* | 3/2013 | Kerth | A61B 5/721 |
| | | | 600/386 |
| 2014/0180158 A1* | 6/2014 | Cheng | A61B 5/6803 |
| | | | 600/544 |
| 2016/0157777 A1* | 6/2016 | Attal | A61B 5/6803 |
| | | | 600/301 |
| 2016/0262703 A1* | 9/2016 | MacCallum | A61B 5/04004 |

\* cited by examiner

HEADGEAR FOR DRY ELECTROENCEPHALOGRAM SENSORS

CROSS REFERENCE TO RELATED APPLICATIONS

This application is a continuation-in-part of U.S. patent application Ser. No. 15/300,992 filed Sep. 30, 2016.

GOVERNMENT LICENSE RIGHTS

This invention was made with Government support under Contract W31P4Q-13-C-0151 awarded by DARPA. The Government has certain rights to the invention.

BACKGROUND OF THE INVENTION

The invention relates to headgears and mounting apparatuses, specifically devices that enable the rapid and reliable placement of sensors on a subject's head. The focus of this patent is for dry electrode EEG applications, although the invention is broadly applicable to placing any type sensor or transducer on the head of a subject.

Conventional recording of EEG signals predominantly involves the use of wet electrodes that utilize a gel for conduction to the subject's scalp. The wet electrodes can be affixed to the skin either with glue or placed in an elastic cap. In many cases, abrasion of the scalp is necessary. The high conductivity of the gel allows electrical conductivity to permeate through hair and any physical gaps between the surface of the electrode and the surface of the scalp is filled and buffed by the gel's liquidity. As a result, wet electrodes offer a secure, low-impedance electrical connection between the subject and the recording instruments with minimal need for advanced mechanics.

However, the use of electrolytic gels, adhesives and scalp abrasion is often time consuming, irritating and uncomfortable for the subject. In response, dry electrodes, which do not require conductive gels, adhesives, or scalp preparation, have been explored as an alternative. In practice, dry electrodes suffer from numerous usability issues. Although acquiring signals on bare skin (e.g., forehead) is straightforward, most EEG setups also require electrodes to be placed across the entire head and especially over areas with hair. With no gel buffer, dry electrodes depend on mechanically stable and adjustable sensor mounts to secure the sensor on the surface of the subject's head.

Challenges with dry EEG headgears involve the need to conform to the many variations in human head shape and size with a standard design that can be used by all subjects. For a dry EEG headgear to be useful, it must also be simple to apply and remove. The basic approach to constructing a dry EEG headgear is based upon adapting the standard elastic EEG cap, exemplified by Gevins et. al. in U.S. Pat. No. 4,967,038. The elasticity in the cap enables it to stretch and cover different sized heads. However, elastic caps suffer from a numerous problems. Although elastic caps are generally flexible, the generic 'balloon-like' shape does not fully conform well to the exact contours of different head shapes (e.g., 'boxy' heads or dimples), leading to areas where the cap is overly tight and other areas where the cap is loose. In addition, the closed nature of the cap makes adjusting the electrodes difficult in cases where the electrodes are in the wrong position or poorly contacting the scalp. Finally, because the elastic cap has no rigid supports, individual electrodes inside the cap are prone to tipping and misalignment during application.

As a result, more sophisticated designs have been explored that use mechanical headgears with mechanisms to individually place sensors on the head for better performance and reliability. One example is found in U.S. Pat. No. 8,103,328 by Turner et al. where each sensor is mounted on a spring-loaded assembly at the tip of an arm connected to a hinge. The hinging mechanism in the arm helps orient the sensor to the surface of the head and the arm generates pressure that connects the sensor to the head. This system is effective at providing optimized and individual tension for each of the sensors in the array but the overall design is complex and bulky. Each headgear contains multiple joints, springs and other moving parts making the system heavy and expensive.

For a simpler and less expensive design, Trewartha et al. (WO 2008/109699 A2) shows a headgear that contains only a few moving parts. In this design, most of the hinges and springs are replaced with solid arms. Only two pivots are present for rotating two major groups of sensors. Plastic deformation of the arms generates tension without the need for other mechanics of moving parts. However, the design shown by Trewartha imposes severe geometric constraints, especially for EEG applications which involve placement of the sensors at specific locations around the scalp. The headgear includes a left band and a right band that clamp on to the head near a user's temples. While this is effective in securing the headgear to the user, the arrangement biases the locations of the electrodes to the sides of the head—areas that are particularly prone to muscular artifacts. Placement of sensors on the upper half of the head and the back of the head, which is necessary for many research and medical EEG applications, cannot be readily accommodated with this setup.

SUMMARY OF THE INVENTION

The invention provides a headgear for placing sensors on a subject's head comprising: a centerpiece; a plurality of arms attached to and radiating outward and downward from the centerpiece; and sensor tips attached to ends of at least some of the arms; wherein at least one of the plurality of arms is a lower arm that is elastic and/or spring-like; and wherein, when the headgear is placed on the subject's head, the at least one lower arm can reach, by bending outwards, to or beyond the maximum circumference of the subject's head, to thereby provide a reactive force for holding the headgear on the subject's head; wherein the sensor tips are connected to at least some of the arms by a rotating joint that can rotate independently of the respective arm about only an axis that is tangent to an end portion of the respective arm to which the sensor tips are connected by the joint.

The invention further provides a headgear for placing sensors on a subject's head comprising: a centerpiece; a plurality of arms attached to and radiating outward and downward from the centerpiece; wherein at least one arm of said plurality of arms is adapted for clamping onto the subject's head for retaining said headgear on the subject; and sensor tips attached to ends of at least some of the arms; wherein at least one of the plurality of arms is a lower arm that is elastic and/or spring-like; and wherein, when the headgear is placed on the subject's head, the at least one lower arm can reach, by bending outwards, to or beyond the maximum circumference of the subject's head, to thereby provide a reactive force for holding the headgear on the subject's head; wherein said at least one arm that is adapted for clamping contains a pad that is adapted for fitting around the subject's ears; and wherein said pad is split into a plurality of sections so as to form an opening around the subject's ears.

By itself, the headgear forms a geometric diameter that is nominally smaller than the maximum circumference of a subject's head so that when the headgear is placed on the subject's head, at least one of the lower arms is forced to bend outward in order to grasp the scalp and thereby apply the reactive force to generate grasping pressure between the at least one lower arm and the scalp.

In view of the limitations with prior art dry EEG headgear, the headgear of the invention involves a minimum of moving parts and adjustments. In some embodiments, upper arms of shorter lengths also radiate outward from the centerpiece to place more sensors on the upper half of the subject's head and thereby make it possible to approximate a standard EEG 10-20 sensor layout. Because each arm moves independently, the headgear is able to fully conform to different head sizes and geometries. The minimization of moving parts and adjustments means that a user can easily and quickly slide the headgear on with minimal assistance and time.

Further aspects of the invention are described in the following detailed description.

DETAILED DESCRIPTION

Figure 1:
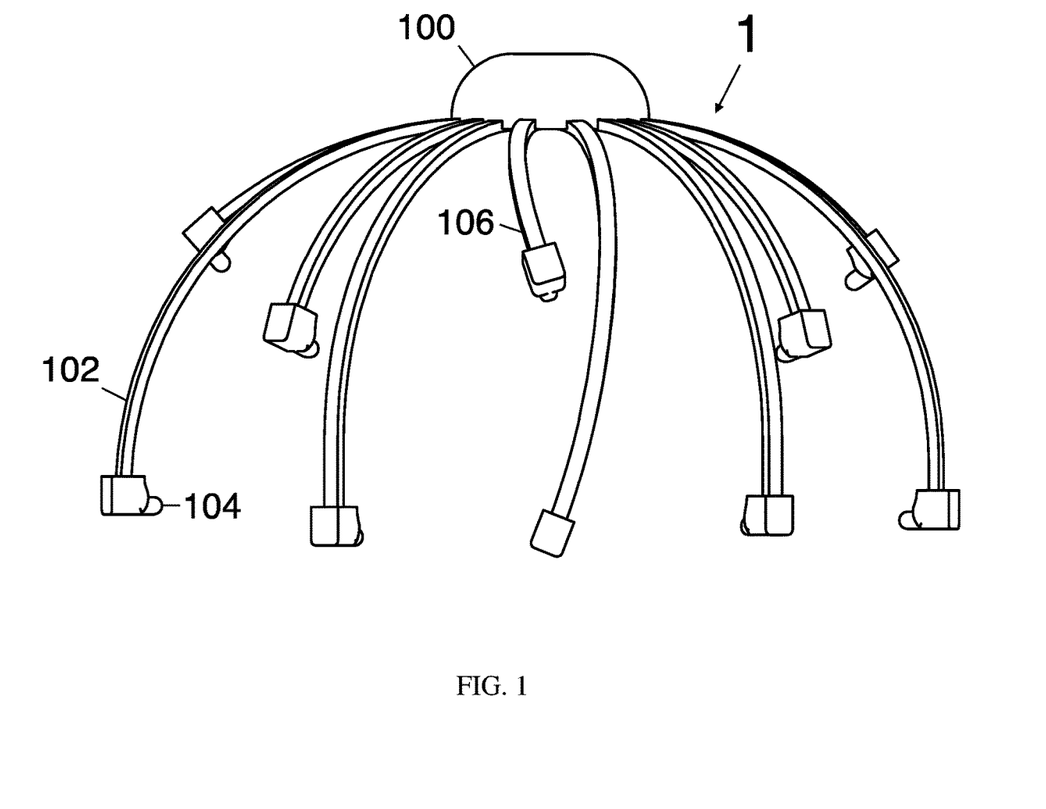
FIG. 1 is a side perspective view of an exemplary embodiment of a headgear according to invention, which shows the major components of the headgear.

Referring to FIG. 1, an exemplary embodiment of a headgear 1 according to the invention includes a centerpiece 100, lower arms 102, sensor tips 104 and an upper arms 106. A preferred embodiment of the headgear 1 contains at least two lower arms 102 and optionally one or more upper arms 106. However, for purposes of clarity, the descriptions below will refer to each generically rather than as specific individual units since embodiments may have multiple, similar copies of each.

The centerpiece 100 provides a reference position for the entire headgear 1. In the exemplary embodiment shown in FIG. 1, the centerpiece 100 is a dome with sufficient interior volume to house the electronics for the headgear 1. The centerpiece is an ideal location for placing electronic components for sensing neurological signals, such as amplifiers, microprocessors, wireless transceivers and control buttons since it is equidistant from all peripheral sensor points and facilitates easy access by the user.

In other embodiments, the centerpiece 100 may be much simpler. In its most basic form, the centerpiece 100 provides a reference position from which a lower arm 102 radiates.

In the embodiments shown herein, all the lower arms 102 and upper arms 106 meet at a single centerpiece 100 because it facilitates placement of approximately the 10-20 EEG electrode array. In other embodiments, different groups of lower arms 102 and/or upper arms 106 may radiate from multiple reference positions provided by multiple centerpieces 100 to provide different sensor layouts optimized for measuring signals at specific areas of the scalp.

The lower arms 102 radiate out and down from the centerpiece 100. The overall diameter formed by all of the sensor tips 104 attached to the lower arms 102 is dimensioned to be smaller than the subject's head. Therefore, when the headgear is placed onto the subject's head, the lower arms 102 are forced to bend and deflect outward in order to accommodate the shape of the head. The action of deflecting the lower arms 102 that hold the sensor tips 104 on the head generates a reactive force that grasps the sensor tips 104 securely to the subject's head.

In some cases, as will be described in greater detail below, the sensor tips 104 may be replaced with alternative structures for grasping the subject's head.

Two important properties of the lower arms 102 are noted. First, the headgear depends on the clamping action of at least one of the lower arms 102 to grasp the subject's head. In the shown exemplary embodiment, the headgear 1 uses an array of similar lower arms 102 for stability. Other possible configurations may include more or less lower arms 102, depending on specific requirements. It is even possible to construct an embodiment that contains only one lower arm 102. In such a case, a rigid, non-springy, support grasps the opposing side of the head. Second, the lower arms 102 must be long enough to reach at least the maximum circumference of the head where there is no upward sloping contour of the head.

More specifically, the lower arm 102 must terminate at a point that enables it to securely hold the headgear 1 onto the user's head. From a geometric standpoint, this point can more precisely be defined by first considering the head as an ovoid, then forming a tangential plane to the ovoid centered at the centerpiece 100. A lower arm 102 extending from the centerpiece 100 also projects a line onto this tangential plane. A second line can then be drawn, from the first line and radiating out from the plane, towards the closest tangent point on the surface of the ovoid.

For the lower arm 102 to adequately grasp the head, it must extend to, or beyond, the critical point where second line becomes perpendicular to the first line and plane. This is the point after which the head starts to "curve away" from the center of the headgear. There is one such critical point for each direction that a lower arm 102 may extend from the centerpiece 100.

Under both of these constraints, the summation of the forces generated by each of the lower arms 102 against the head will be evenly balanced and not generate any upward force on the headgear. If the lower arms 102 are too short to reach the maximum circumference of the head, the interaction between the sensor tips 104 and the sloped surface of the head would generate an upward force whereby the headgear would exhibit a tendency to travel up and off the head.

Figure 2:
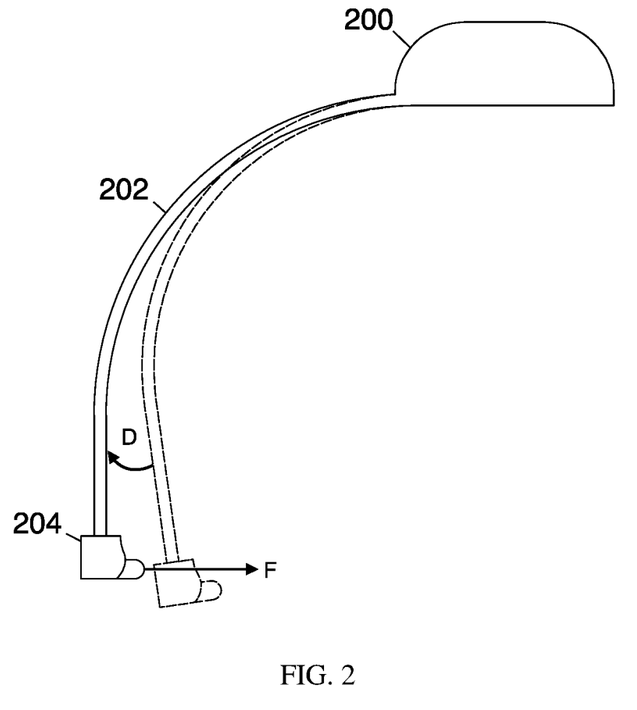
FIG. 2 illustrates the bending of a single lower arm of the headgear shown in FIG. 1

FIG. 2 shows a detail of the deflection process in the lower arm 202. The initial state of the lower arm 202 is illustrated in the dotted lines. Bending the lower arm 202 outwards in the direction D causes a reactive force F due to the elastic and/or spring-like deformation of the lower arm 202. When the headgear is placed on a subject's head, the reactive force F causes the sensor tips 204 to grasp the scalp sufficiently to form a connection that enables sensing or transduction.

In the exemplary embodiment of the invention, the sensor tip 204 is formed as a cylindrical knob, coated with an Ag/AgCl material to serve as a dry EEG electrode. Broadly speaking, the invention is not limited to any specific electrode or contact design. Another embodiment of the invention may use a set of pins or other dry electrode design. Alternatively the sensor tips 204 need not be dry or even an EEG electrode. As an example, a wet EEG headgear may be constructed by placing saline soaked foam at the sensor tips 204. It is also possible to build a fNIRS (functional near-infrared spectroscopy) headgear by mounting optical transducers and detectors on the sensor tips 204. Finally, alternative embodiments of the invention may mix and match different types of sensors and transducers in accordance with the application and position.

In the exemplary embodiment shown in FIG. 2, the sensor tip 204 is a single continuous piece of material that is integral with the lower arms 202. In other embodiments, it may be preferable to connect the sensor tips 204 to the lower arms 202 with a joint (not shown) that is capable of pivoting, rotating or moving to better align the sensor tips 204 with the local geometry of the user's head. Additionally, the joint may be spring-loaded for more conformability. In alternative embodiments an attachment mechanism is included to enable the sensor tips 204 to be removed from the lower arms 202.

Figure 3:
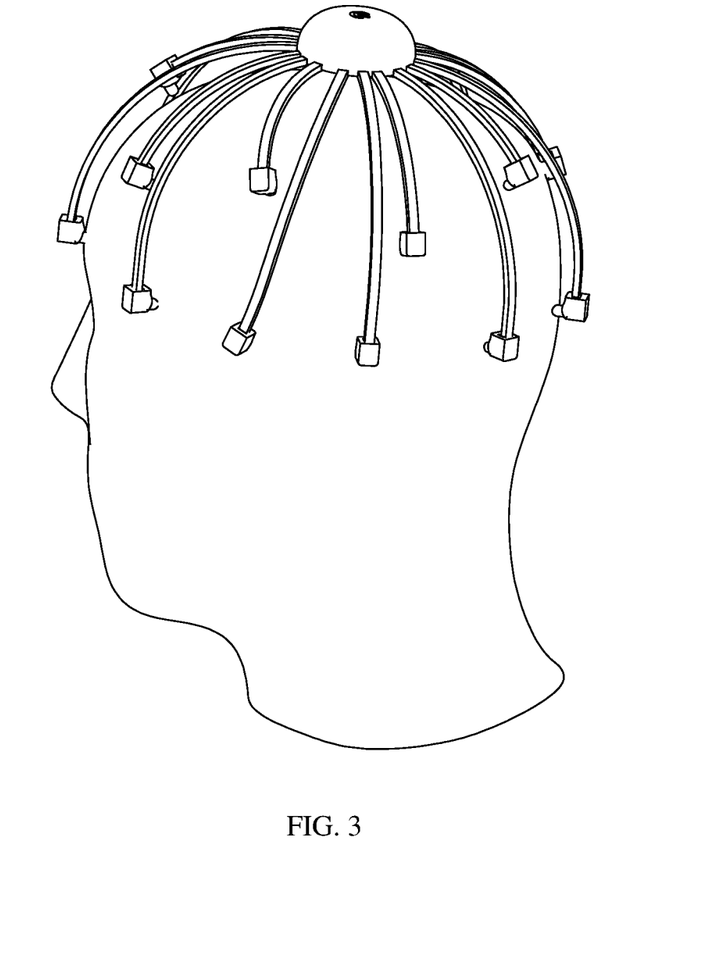
FIG. 3 is an illustration the exemplary embodiment of the headgear shown in FIG. 1, as placed on a subject's head.

FIG. 3 shows an exemplary embodiment of the headgear when placed on a human head. The array of lower arms and upper arms radiating from a centerpiece approximates the standard 10-20 EEG electrode placements. Other embodiments of the invention can accommodate different types of sensor placements in accordance with the particular sensing application.

Referring again to FIG. 1, the upper arms 106 are used to more broadly place sensors on the head, not just at the circumferential locations enabled by the lower arms 102. The upper arms 106 likewise terminate in sensor tips 104 but are shorter to cover additional scalp locations above the maximum circumference. The difference, however, is that the upper arms 106 cause the sensor tips that are attached thereto to contact a sloped area of the head, which in turn generates an upward reactive force on the headgear as a whole. Since the upper arms 106 do not provide a direct counteracting force, such as provided by the lower arms 102, the upward reactive force generated by contacting the upward sloped area of the head can act to push the headgear 1 up and away from the head. Therefore, embodiments that utilize upper arms 106 must be so designed that the lower arms 102 generate sufficient clamping force to counteract the upward force generated by placement of the upper arms 106 on the upward sloped area of the head.

In some embodiments, it is useful to vary the geometric cross section of the upper arms 106 and lower arms 102 to minimize the upward force generated by the upper arms 106 while maximizing the clamping force of the lower arms 102 to best stabilize the headset on the subject. For example, the upper arms 106 can be dimensioned to have a thinner profile than the lower arms 102. Another example could employ a more elastic material for the upper arms 106 versus the lower arms 102.

In some embodiments, extra arms (not shown) are included for generating additional frictional force to help counteract the upward reactive force generated by placement of the upper arms 106 on the upward sloped area of the head. One example involves placing extra lower arms 102 that have large pads, instead of sensor tips attached to the dorsal ends, in order to generate a frictional force.

In other embodiments of the invention, only the upper arms 106 include sensor tips 104 and the lower arms 102 are used only for grasping the subject's head. In general, it is possible to mix and match different combinations of tips: sensors and grasping pads to suit a particular application. It is also possible to mix and match different sensors in the same headgear. For example, an application may call for placing optical $SpO_2$ sensors on the forehead arms and EEG sensors at the remaining locations.

Figure 4:
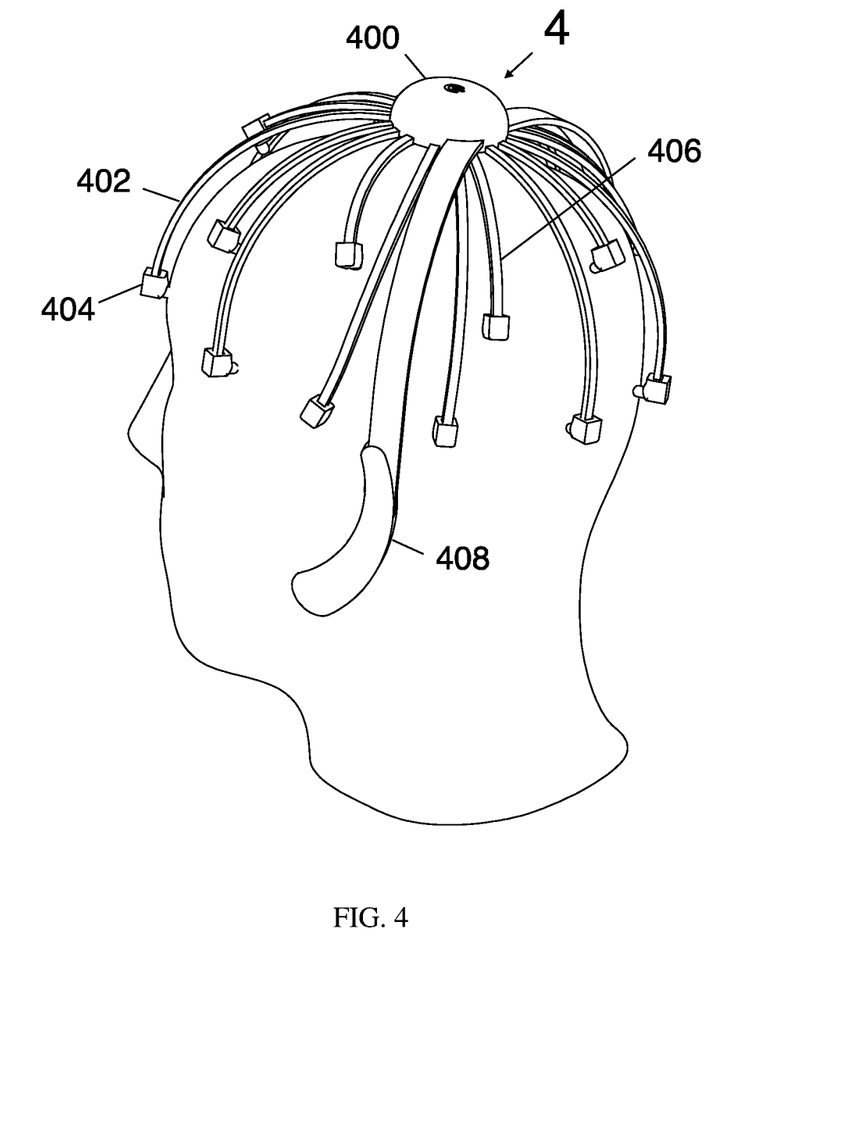
FIG. 4 is an illustration of another exemplary embodiment of the a headgear according to invention, including lower arms that grip behind the ears and sensor tips that provide extra conformance to the subject's head.

Referring to FIG. 4, another exemplary embodiment utilizes an ear grip 408 that contacts the areas of the head adjacent to the subject's ears for extra stability. Using the area around the ears is particularly advantageous since it presents a large, relatively flat, surface area for distributing contact pressure. A headphone-like, circumaural cup is an example of an ear grip and may be used in some embodiments of the invention. However a full headphone-type ear cup presents several drawbacks. An ear cup limits hearing and may also interfere with certain sensor positions near the temples, such as T3 or T4 (in the international 10-20 convention). Embodiments of the invention may preferentially use a partial ear cup that does not fully surround and/or cover the ears to overcome the above limitations.

The ear grip 408 shown in the embodiment of FIG. 4 also illustrates a second key retaining mechanism for holding the device on to the subject's head. Whereas the lower arms 102 (shown in the embodiment of FIG. 1), operate primarily on the basis of a frictional grasping force by holding onto scalp locations along or below the maximum circumference of the head, the ear grip also employs a hooking action (in addition to some degree of frictional force) by resting around and under the lower surfaces the head that are beyond the maximum circumference.

Figure 5:
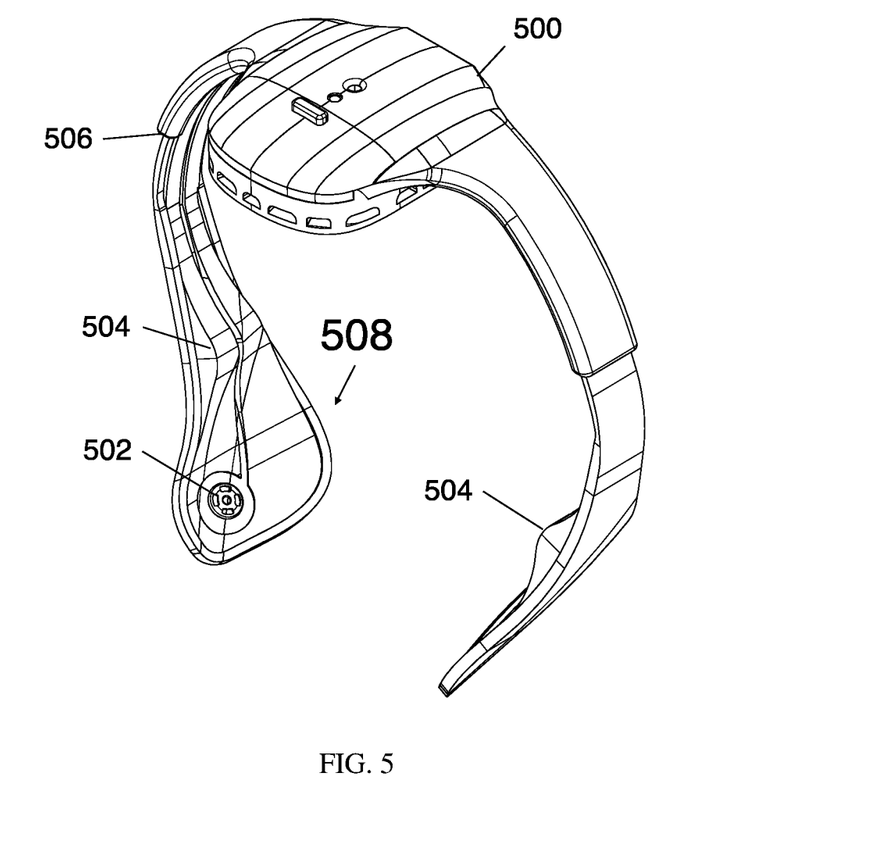
FIG. 5 is an illustration of still another exemplary embodiment of a headgear according to the invention, showing the centerpiece and the ear bands that grip behind the ears. The other lower and upper arms are omitted for purposes of clarity.

Referring to FIG. 5, an ear band 508 is used as a variant of the ear grip 408. In this case, the ear band 508 is based on the same basic concept of the ear grip 408, but only spans the surfaces around the posterior of the ear, near the mastoid. The area behind the ear and mastoid is useful since it contains few muscles and joints, and thereby minimizes movement of the headgear. This location also allows the lower half of the ear band 508 to rest on the underside of the subject's head and use a hooking action for keeping the system from moving up and off the user.

A detailed diagram of a specific ear band 508 embodiment is shown in FIG. 5, without any of the other lower or upper arm types for purposes of clarity. The structure can be considered another type of lower arm but additionally optimized for holding the headset on to the head rather than for only holding a sensor. Like most types of lower arms, the ear band 508 emanates from the centerpiece 500 and contains a sensor 502 mounted for measuring signals from the subject's mastoid. In contrast to the lower arms previously described, however, the primary purpose of the ear band 508 is to provide stability and hence contains extra surface area around the sensor 502 for distributing contact pressure across a large portion of the head. In this embodiment, the ear band 508 also contains a sliding joint 506 to enable the user to adjust the length for optimal placement on the head. A contour 504 is also used to better match the surface of the ear band 508 to the surface of the head.

The ear band 508 supplies the majority of the retaining force for the headgear 1 to thereby improve the subject's comfort.

Figure 6:
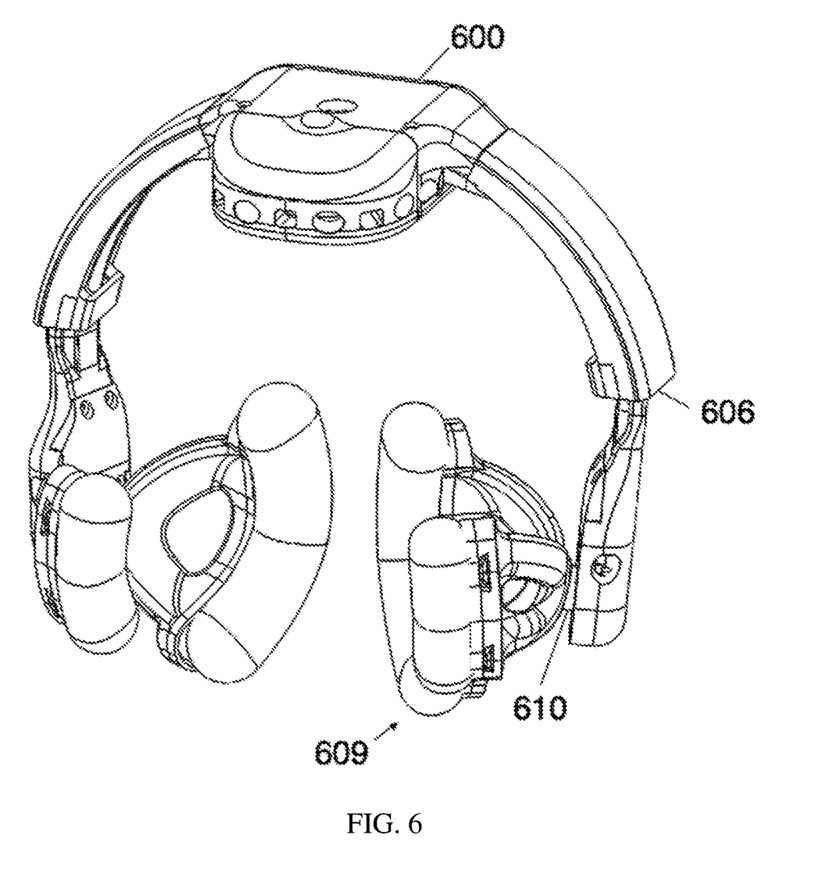
FIG. 6 is an illustration of still another exemplary embodiment of the headgear according to the invention, showing the centerpiece and the pads that grip both in front and behind the ears without fully covering the subject's ears. The other lower and upper arms are omitted for clarity.

FIG. 6 shows another embodiment of headgear utilizing a set of ear pads to grip around, but not fully covering the subject's ears. As with FIG. 5, the upper or lower arms have not been drawn for purposes of clarity. As with the other embodiments, the headgear starts with a centerpiece 600. A sliding joint 606 controls the distance of the entire ear pad assembly 609 with respect to the centerpiece 600 to better match different head sizes. The ear pad assembly 609 rests on a pivoting hinge 610 to better conform to difference different head contours.

It is worth noting that other embodiments of the invention may use a different geometric arrangement of pads. For example, rather than a front and rear pad, an alternative embodiment may use a top pad and a bottom pad to grip around the ears while still preserving an open space over the subject's ears.

Figure 7:
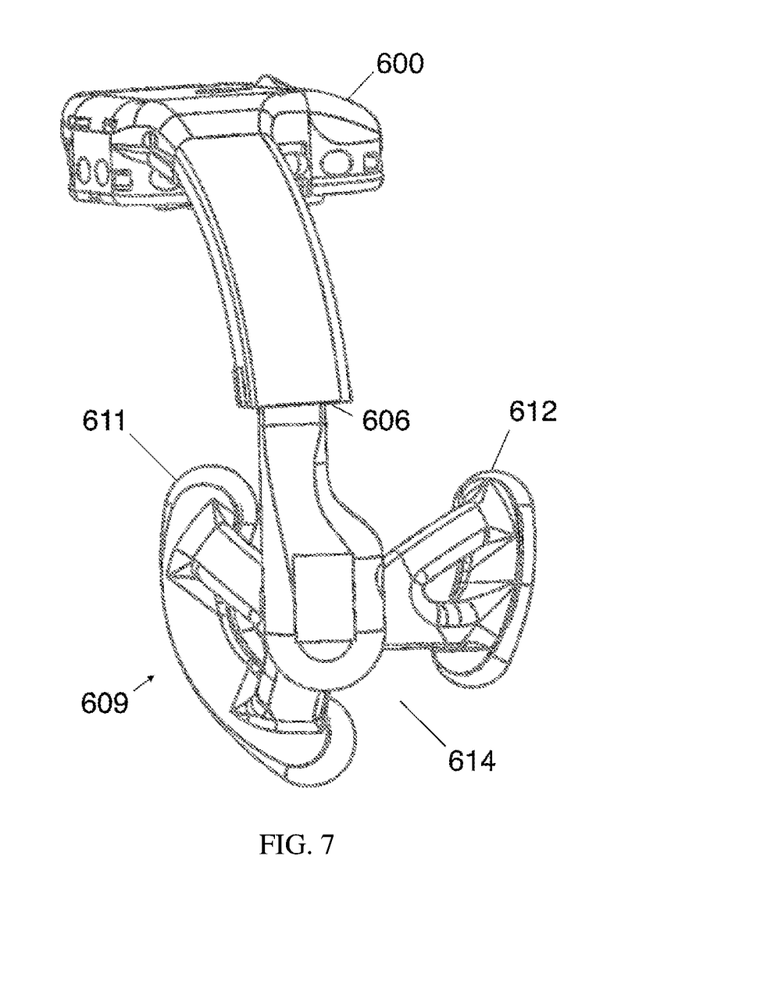
FIG. 7 is a side illustration of the embodiment shown in FIG. 6. The pads on the opposing side of the centerpiece are omitted for clarity.

A side view of the ear pad assembly 609 is shown in FIG. 7. The ear pad assembly 609 consists of a rear pad 611 and a front pad 612. Compared to the previous ear band embodiment, two pads provide additional stability compared to a single ear band behind the ear. At the same time, separating the rear pad 611 and front pad 612 preserves an open space 614 to keep the subject's ears relatively exposed. This allows the subject to maintain hearing and keeps the area clear for the placement of additional sensors (e.g., T3/T4 or A1/A2).

It is also worth noting that other embodiments of the invention may also utilize other variants of lower arm shapes to grasp or hook onto other areas of the head for stabilizing the headgear. In general, any surface of the head or body below the maximum circumference of the head is suitable, such as the chin. Using extra sets of lower arms, which are primarily optimized for grasping or hooking, is advantageous in many cases since it allows the other lower arms, which are used for sensing, to contact the subject's head with minimal pressure for ensuring comfort.

Figure 8:
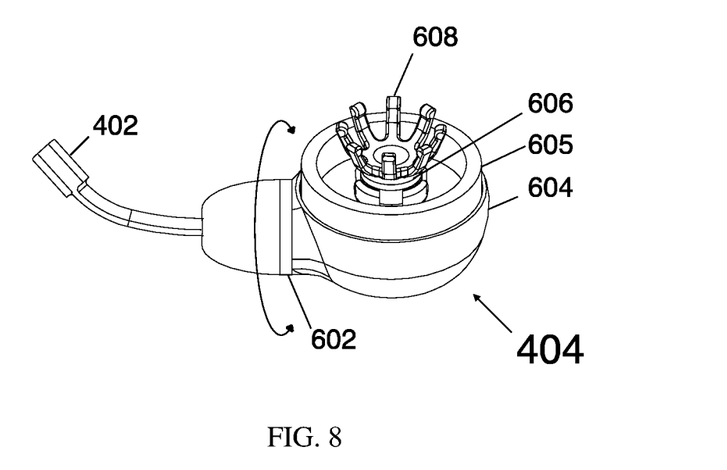
FIG. 8 is an illustration of an alternative embodiment of the sensor tip assembly to the embodiment shown in FIG. 4. The embodiment of FIG. 8, has the ability to rotate with respect to the leg, allows the sensor to move and tilt independently for improved conformance to the subject, and contains an actively driven shield.

FIG. 8 shows a more sophisticated embodiment of the sensor tip 404 used in the embodiment of FIG. 4. The embodiment shown in FIG. 8 adds extra degrees of freedom for complex electrodes. Whereas the sensor tip 104 used in embodiment of FIG. 1 is a simple structure that functions directly as the sensing electrode, the sensor tip 404 contains multiple parts to optimally place an electrode 608 that is separate from the main body referred to collectively as the sensor tip 404.

Figure 9:
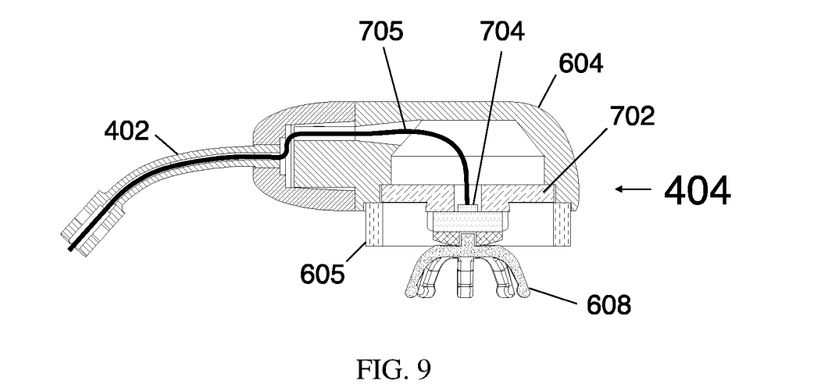
FIG. 9 is a cross-section of the sensor tip shown in FIG. 8.
Figure 10:
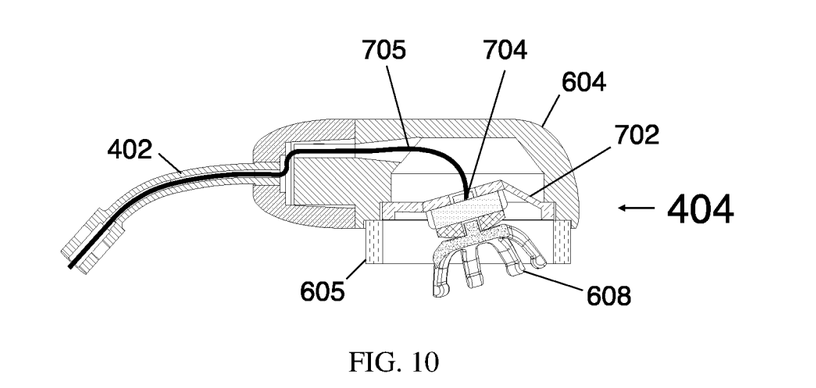
FIG. 10 is a cross-section of the sensor tip shown in FIG. 9 showing the electrode tilting with respect to the sensor tip.

In this embodiment, the sensor tip 404 is connected to the lower arm 402 via a rotating joint 602. This allows the electrode 608, which is connected via the receptacle 606, to better align with the surface of the subject's head by providing an extra degree of freedom. This is especially important when the headgear is used with dry electrodes due to their rigidity and need for conformance with the surface of the subject's head. In addition, the sensor tip 404 contains a conductive shield 604 that covers, and extends around the sides of the electrode 608 to provide extra electromagnetic shielding against external interference. For dry electrode applications, it is best to incorporate a local active amplifier 704 within the sensor tip 404, preferably right above the electrode 608, as shown in FIGS. 9 and 10, to buffer the high impedance signal from the electrode 608 and provide a low impedance signal output. The local active amplifier 704 can be further used to drive a conductive shield 604. Optimally, the shield 604 will surround the electrode in all directions that are not facing the subject for maximum protection against external interference. For space constrained implementations, a reduced shield geometry is also possible (e.g., only the top of the electrode 608, rather than surrounding the side). A local active amplifier also simplifies shielding since the wire 705 connecting the sensor tip 404 back to the main electronics of the headgear does not need to be shielded.

Optionally, a cushion 605 can also be placed around the electrode 608 to help improve subject comfort. The cushion 604 relieves excess pressure (e.g., on large heads) when the electrode 608 is forced into the interior of the sensor tip 404. The cushion also prevents the electrode 608 from hitting the subject's head in cases when the sensor tip 404 is misaligned with the surface of the subject's head.

A cross-sectional view of the sensor tip 404 of the embodiment of FIG. 8 is shown in FIG. 9. To provide for extra conformance to the subject, the electrode 608 is mounted on a flexible element 702, and is thereby adapted for aligning the electrode to the surface of the subject's head when the sensor tip 404 is placed onto the subject's head.

This provides yet another extra degree of freedom by allowing the electrode 608 to tilt and align with the irregular surfaces of the scalp. FIG. 10 shows an example of how stretching the flexible element 702 tilts the electrode 608. In the embodiment, the flexible element 702 is made from a flat spring. Other materials and designs are possible including using a spring or suspending the electrode 608 on a membrane. The flexible element 702 has the additional benefit of mitigating some movement artifacts by dampening vibrational forces from the headset. As with the rotating joint 602, this extra degree of freedom is important for dry electrodes which must conform to the subject's head for optimal comfort and signal quality.

In the embodiments described previously, all electrodes within the headgear have been located at the tips of flexible arms. However, it may also be necessary to place a single, or multiple, electrodes underneath the centerpiece (e.g., the Cz location at the crown of the head). Simply mounting an electrode underneath the centerpiece is problematic since it is easy for the pressure on the electrode to the scalp to vary greatly depending on small changes in the vertical position of the headset with respect to the subject's head resulting in discomfort and/or loss of signal.

Figure 11:
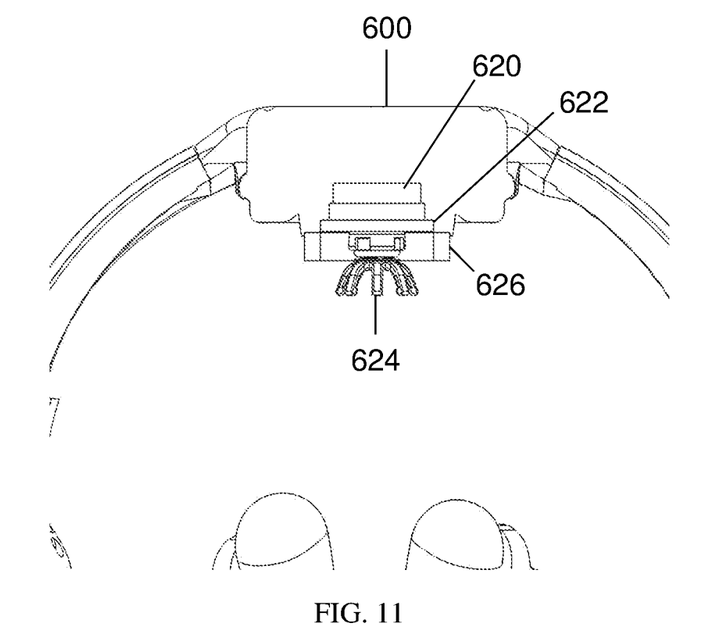
FIG. 11 is a cross section of an embodiment of the headgear showing the mounting of a sensor directly underneath the centerpiece.
Figure 12:
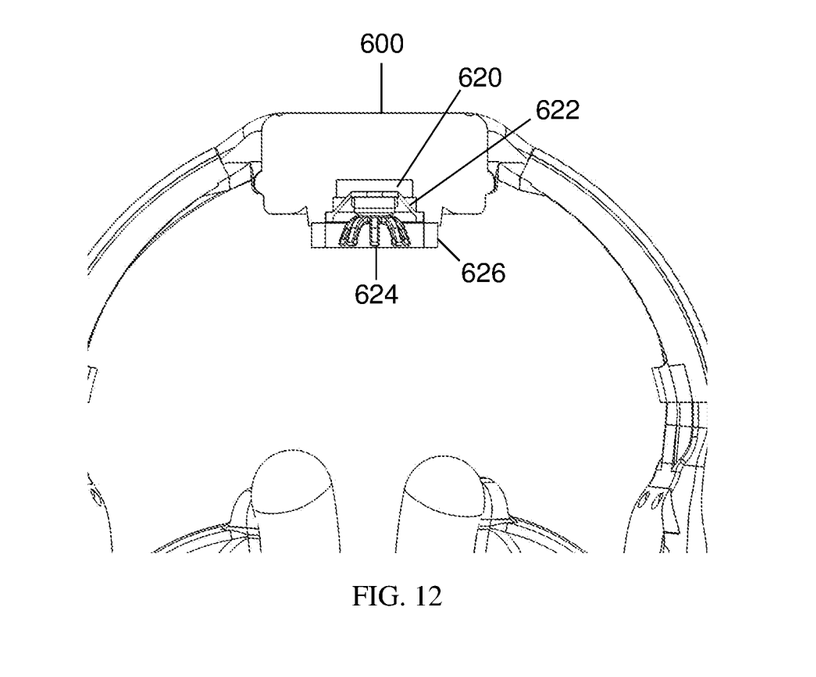
FIG. 12 is the same view as FIG. 11 showing the sensor being forced into the interior of the centerpiece.

In FIG. 11, a cross section of the embodiment in FIG. 6 is shown, with an emphasis on the area around the centerpiece 600. An electrode 624 is located underneath a hollow cavity 620 within the body of the centerpiece 600. The electrode is mounted on top of a membrane of flat spring 622. When the headgear is placed on the subjects head, the electrode 624 is forced into the hollow cavity 620 by stretching the membrane or flat spring 622, as shown in FIG. 12. This provides the electrode 624 mounted underneath the centerpiece 600 a degree of mechanical flexibility and immunity to relative shifts in headset position for more reliable contact. At the same time, a cushion 626 can be optionally placed around the electrode 624 for subject comfort in case the headgear is pushed down hard onto the subject's head.

Alternative embodiments of the invention may use a coil spring or foam in place of the membrane/flat spring 622.

In the exemplary embodiment shown, the headgear 1 is made primarily out of ABS plastic. Manufacturing the headgear 1 out of a single piece of plastic greatly simplifies the production process and lowers cost although it is possible to also make the headgear from separate pieces joined together. Other embodiments may include other materials that are capable of elastic deformation such as metal spring wires. It may also be advantageous to mix and match materials to provide a mix of mechanical properties. As an example, the upper arms may be made out of a more flexible material (e.g., nylon) than the lower arms (e.g., ABS or metal) to reduce the amount of undesired upward reactive force. In some cases, the headgear is made to be nominally conductive by using metal or a specially treated plastic in order to provide an electromagnetic shield for reducing interference noise.

The benefits specifically stated herein do not necessarily apply to every conceivable embodiment of the present invention. Further, such stated benefits of the present invention are only examples and should not be construed as the only benefits of the present invention.

While the above description contains many specificities, these specificities are not to be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A headgear for placing sensors on a subject's head comprising:
   a centerpiece;
   a plurality of arms attached to and radiating outward and downward from the centerpiece; and
   sensor tips attached to ends of at least some of the arms;
   wherein at least one of the plurality of arms is a lower arm that is elastic and/or spring-like; and
   wherein, when the headgear is placed on the subject's head, the at least one lower arm can reach, by bending outwards, to or beyond the maximum circumference of the subject's head, to thereby provide a reactive force for holding the headgear on the subject's head;
   wherein the sensor tips are connected to at least some of the arms by a rotating joint that can rotate independently of the respective arm about only an axis that is tangent to an end portion of the respective arm to which the sensor tips are connected by the joint.

2. The headgear of claim 1, wherein at least one of the plurality of arms is an upper arm that is disposed for placing a sensor tip at a location above the maximum circumference of the subject's head.

3. The headgear of claim 2, wherein the geometric cross-section of a plurality of said upper arms is dimensioned to provide less reactive force than the geometric cross-section of a plurality of said lower arms for better retaining the headgear on the subject's head.

4. The headgear of claim 1, further comprising an electrode disposed underneath the centerpiece.

5. The headgear of claim 4, wherein the electrode disposed underneath the centerpiece is so disposed as to be forced into a cavity within the centerpiece when the headgear is placed onto the subject's head.

6. The headgear of claim 1 wherein at least one of said sensor tips contains an electrode mounted on a flexible element that is adapted for aligning the electrode to the surface of the subject's head when said at least one sensor tip is placed onto the subject's head.

7. The headgear of claim 6, wherein said at least one sensor tip further compromise an active amplifier connected to the electrode for buffering a signal from the electrode.

8. The headgear of claim 7 wherein said amplifier is adapted to drive a conductive shield surrounding the surfaces of the electrode not facing the subject's head.

9. The headgear of claim 1, wherein at least one arm of said plurality of arms is adapted for clamping onto the subject's head for retaining said headgear on the subject.

10. The headgear of claim 9, wherein the length of said at least one arm that is adapted for clamping is adjustable for better adapting to the subject's head.

11. The headgear of claim 9, wherein said at least one arm that is adapted for clamping contains a pad that is adapted for fitting around the subject's ears.

12. The headgear of claim 9, wherein said at least one arm that is adapted for clamping is also adapted to supply the majority of the retaining force for the headgear to thereby improve the subject's comfort.

13. A headgear for placing sensors on a subject's head comprising:
    a centerpiece;
    a plurality of arms attached to and radiating outward and downward from the centerpiece;
    wherein at least one arm of said plurality of arms is adapted for clamping onto the subject's head for retaining said headgear on the subject; and
    sensor tips attached to ends of at least some of the arms;
    wherein at least one of the plurality of arms is a lower arm that is elastic and/or spring-like; and
    wherein, when the headgear is placed on the subject's head, the at least one lower arm can reach, by bending outwards, to or beyond the maximum circumference of the subject's head, to thereby provide a reactive force for holding the headgear on the subject's head;
    wherein said at least one arm that is adapted for clamping contains a pad that is adapted for fitting around the subject's ears; and
    wherein said pad is split into a plurality of sections so as to form an opening around the subject's ears.

14. The headgear of claim 13, wherein said plurality of pads comprise a front pad and a rear pad so as to form an opening around the subject's ears.

15. The headgear of claim 13, wherein the sensor tips are connected to at least some of the arms by a rotating joint that can rotate independently of the respective arm about an axis that is tangent to an end portion of the respective arm to which the sensor tips are connected by the joint.

* * * * *